United States Patent [19]

Perser et al.

[11] 4,176,459
[45] Dec. 4, 1979

[54] FOOT ELEVATION MEASURING DEVICE

[75] Inventors: Donald A. Perser, Northbrook; Donald A. Roman, Des Plaines, both of Ill.

[73] Assignee: Ballert Orthopedic Corp., Chicago, Ill.

[21] Appl. No.: 564,845

[22] Filed: Apr. 3, 1975

[51] Int. Cl.² ............................ G01B 3/30; A61F 3/00
[52] U.S. Cl. .................................... 33/174 D; 33/3 R; 128/80 DB
[58] Field of Search ............ 33/174 D, 174 H, 168 R, 33/3 R, 174 R; 128/581, 80 R, 68, DIG. 15, 80 DB; 36/71; 3/4 R, 5

[56] References Cited
U.S. PATENT DOCUMENTS 3,640,273 2/1972 Ray .............................. 128/DIG. 15
3,758,891 9/1973 Geister ........................................ 3/5

Primary Examiner—Willis Little
Attorney, Agent, or Firm—Ronald A. Sandler

[57] ABSTRACT

The present invention relates to a measuring device for measuring the relative-correctable difference in length of a person's legs in order to determine the amount of elevation required in the construction of an orthopedic shoe to compensate for such difference. The measuring device includes a base plate of predetermined thickness and a sole plate of predetermined thickness, the sole plate having a plan configuration similar to the base plate. Means are provided for preventing relative movement of the sole plate and the base plate, and means for securing the base plate and the sole plate to the foot of the associated person is provided whereby such person can stand and walk on the measuring device. Additional measuring plates of predetermined thickness are provided for increasing the elevation of the measuring device in predetermined increments whereby the correctable difference in elevation of the associated person's leg can be determined.

17 Claims, 7 Drawing Figures

U.S. Patent     Dec. 4, 1979     4,176,459
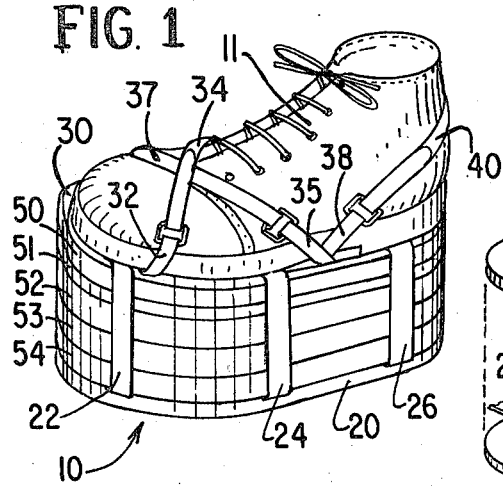
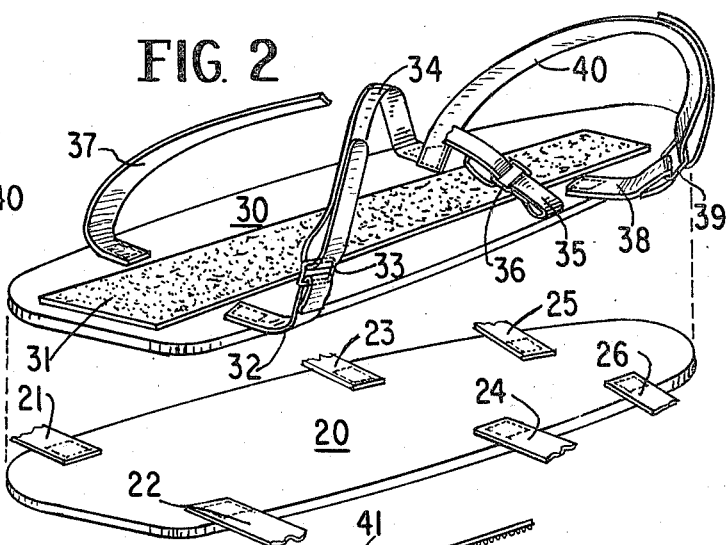
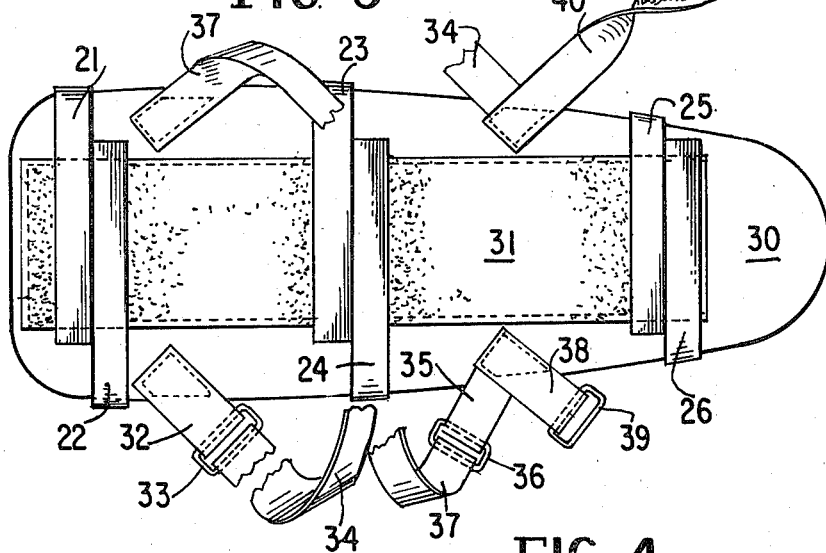
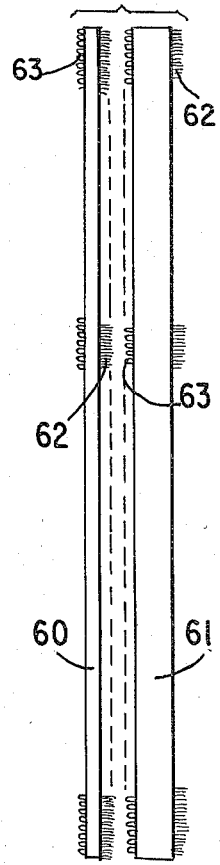
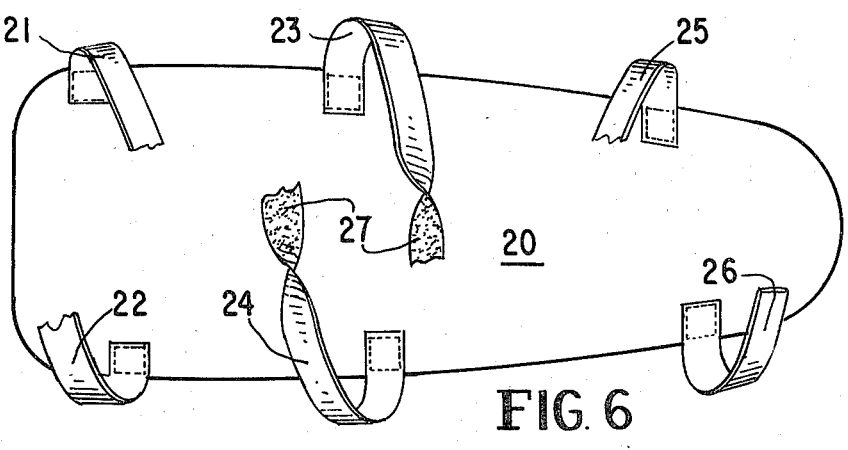

FOOT ELEVATION MEASURING DEVICE

This invention relates to a measuring device and has more specific application to the provision of a measuring device to determine the amount of elevation required in an orthopedic shoe in order to compensate for the difference in length of the wearer's legs.

The condition of uneven leg length is frequently encountered, and may be caused by accident or illness or be prenatal in origin. In such circumstances, the handicapped person generally engages the services of an orthopedist, brace technician or an orthopedic shoe technician. A specially constructed shoe may be required in order to compensate for the difference in leg length so that the legs will be functionally even. Frequently this difference in elevation is determined by very crude methods, such as the placing of books or blocks under the foot of the individual, but in such instances, because such blocks can not be properly adjusted in elevation, or because they may not be fastened to the foot of the wearer so as to allow that person to walk and allow the technician to observe the effect of the elevated height on the person's gait, such techniques are generally unsatisfactory and frequently require the rebuilding of the special shoe after initial construction.

Other devices attempting to provide a more specific measurement have been proposed, such as that in Benesch U.S. Pat. No. 3,419,961; however, such device would appear not to be commercially satisfactory because it appears to be cumbersome and difficult to use.

It is a principal object of the present invention to provide a measuring device simple in construction and operation, yet which device will furnish the technician with the necessary accuracy to allow him to properly determine the correctable difference in leg length with reasonable accuracy.

It is a further object of the invention to provide easily detachable means for securing of the measuring device to the person's foot, whereby the technician can promptly remove the measuring device and provide adjustments in its elevation.

A further advantage of the present invention lies in the provision of a measuring device which can be attached to the foot of the wearer, enabling him to walk with the measuring device and enabling the technician to observe the posture and gait of the person, in order to properly determine the measurement and further refine same, if necessary.

Accordingly, it is a primary object of the invention to provide a device for measuring the relative correctable difference in an individual's leg lengths, such device comprising a base plate of predetermined thickness, at least one sole plate of predetermined thickness and having a plan configuration similar to the base plate and being positionable in an overlying relationship relative thereto. Means for preventing relative movement of the sole plate and the base plate is provided; and means for securing the base plate and the sole plate to the foot of the associated person also is provided, whereby the person can stand and walk thereon and whereby a technician by computing the elevation of the base plate and the sole plate can determine the correctable difference in elevation of the associated person's legs.

An important object of the invention is to provide intermediate measuring plates to be disposed between the base plate and sole plate, whereby the elevation of the measuring device can be increased in predetermined increments.

Still another object of the invention is to provide those measuring plates in different colors for different thicknesses, whereby through visual observation and mental computation the technician can determine the existing elevation of the measuring device without actually measuring same.

The invention, both as to its organization and method of operation, together with further objects and advantages thereof, will best be understood by reference to the following specification taken in connection with the accompanying drawings, in which:

FIG. 1 is a perspective view of an assembled measuring device secured to a shoe which might be worn on the shorter leg of the person whose leg is to be measured for corrective shoes, and illustrates generally the features of the invention;

FIG. 2 is an exploded perspective view of the measuring device and demonstrates the relative positions of certain parts thereof;

FIG. 3 is a plan view of an assembled measuring device illustrating the position of the various connecting means and embodying the preferred features of the invention;

FIGS. 4 and 5 are side elevational views of typical measuring plates used in the measuring device as shown in FIG. 1.

FIG. 6 is a plan view of the base plate shown in perspective in FIG. 2, for use with the measuring device; and FIG. 7 is a side elevational view of an alternate embodiment of the invention, wherein different means are provided for preventing relative movement of the various plates to one another.

Referring now more particularly to FIGS. 1 through 3 of the drawings, there is illustrated a measuring device designated generally as 10, secured to a shoe 11 of the person whose difference in leg length is to be determined.

The measuring device 10 consists generally of a base plate 20, a sole plate 30 by which the device is secured to the shoe 11, a plurality of measuring plates 50 through 54 disposed between the base plate 20 and the sole plate 30, and holding means to be described hereinafter for preventing a relative movement of the measuring plates 50-54, the sole plate 30 and the base plate 20 relative to one another, as well as binding means to be described hereinafter for detachably securing the assembled measuring device to the shoe 11 of the associated person.

Referring now more particularly to FIGS. 2 and 6, the construction of the base plate 20 is seen in greater detail. The base plate 20 comprises a plate of predetermined thickness generally matching in plan view the shape of the sole of a shoe, being larger toward the forward or toe portion and tapering to a narrower heel portion.

The base plate 20 includes holding means thereon for securing it to the sole plate 30 and for preventing relative movement therebetween; also, when one or more of the measuring plates 50-54 is disposed therebetween, such holding means also prevents relative movement of the measuring plates relative to the base plate 20 or sole plate 30.

As best seen in FIG. 6, the holding means comprises a pair of cooperating front holding straps 21 and 22 which are sewn to the opposite side edges of the base plate 20. As best seen in FIG. 6, the straps 21 and 22 are offset lengthwise from one another by the width of a strap, whereby when the straps are in an overlying position relative to the sole plate 30 (FIG. 3) they will not interfere with one another when detachably secured to the sole plate.

A pair of middle holding straps 23 and 24 also is provided, also being offset like the front straps 21 and 22, and finally a third pair of holding straps 25 and 26 is disposed toward the rear of the base plate 20.

Each of the straps 21 through 26 has on the inner surface thereof one portion of a two-portion adherent material, such as that sold under the trade name "Velcro", adapted to cooperate with an appropriately positioned complementary portion of Velcro material disposed on the sole plate 30, the Velcro material being designated as 27 on typical holding straps 23, 24.

The sole plate 30 includes a pad 31 of complementary Velcro material, whereby overlying the respective pairs of holding straps 21 through 26 onto the pad 31, in the positions illustrated in FIG. 3, the sole plate 30 and the base plate 20 (as well as any measuring plates 50–54) are detachably assembled together and are prevented from moving relative to one another.

The sole plate 30 also is of a predetermined thickness and is similar in plan configuration to the base plate 20. When a technician desires to determine the correctable difference in elevation between the legs of an individual, by knowing in advance the predetermined thickness of the sole plate and the base plate, the technician knows immediately one portion of the total difference in leg length.

In order to determine the exact compensating difference required in the final shoe, a plurality of measuring plates 50 through 54 is provided. Each of the measuring plates is similar in plan configuration to the base plate 20 and each is of a predetermined thickness. As best illustrated in FIGS. 4 and 5, the measuring plates 50–54 preferably are of varying predetermined thicknesses, starting in ⅛" increments and going up to ½" thick increments. By inserting the appropriate measuring plates between the base plate 20 and the sole plate 30, and thereafter placing the holding straps 21 through 26 in their connected position, as illustrated in FIGS. 1 and 3, the measuring plates are prevented from movement relative to the base plate 20 and the sole plate 30 and allow the technician to elevate the measuring device in predetermined increments.

In the preferred embodiment, the base plate is ¼" thick, while the measuring plates start in ⅛" thicknesses and may increase in ⅛" increments up to ½" thick plates. To facilitate the work of the technician, each predetermined thickness of measuring plate is composed of a different color composition (e.g. all ⅛" plates black, ¼" plates green, ⅜" plates red, etc.) whereby through visual examination and quick mental calculation the technician is able to quickly compute the total elevation of the measuring device 10 at any one time.

In order to detachably secure the measuring device to the foot of the person, appropriate binding straps are provided on the sole plate 30. In the preferred embodiment illustrated, there are provided along one side of the sole plate 30 a toe strap 32, ankle strap 35 and heel strap 38, each having fixedly secured thereto an appropriate loop 33, 36 and 39, respectively. Fixedly secured to the opposite sides of the sole plate 30 are cooperating strap members 34, 37 and 40, respectively.

As best seen in FIGS. 1 and 2, the straps 34 and 35 are disposed opposite one another on the sole plate, while the straps 32 and 37 are disposed opposite one another, although in operation these straps are intended to crisscross, as illustrated in FIG. 1, whereby strap 34 is intended to pass through the loop 33 on strap 32, while strap 37 is intended to pass through the loop 36 on strap 35, thereby to more securely bind the measuring device to the shoe. The heel straps 38 and 40 are adapted to be engaged behind the heel portion of the shoe, as illustrated in FIG. 1.

Each of the straps 34, 37 and 40 includes along most of the outer surface thereof a first Velcro material 41. The outer end portion of each of said straps, however, includes on the outer surface thereof the cooperating Velcro material 42 (FIG. 3). By inserting the ends of the straps 34, 37 and 40 through the respective loops 33, 36 and 39 and pulling thereon, the greatest tightening of the measuring device relative to the shoe 11 can be accomplished. By folding over the outer end of each strap and placing it on the remainder of the strap, the cooperating Velcro portions 41 and 42 operate to detachably secure such strap in position.

It should be understood that if it is desired to eliminate the loops 33, 36 and 39, then the cooperating Velcro material 42, rather than being disposed on the outer edge portions of the straps 34, 37 and 40, could be disposed on the outer surfaces of the straps 32, 35 and 38.

In FIG. 7, there is illustrated an alternate method of holding means for preventing relative movement of the sole plate 30 relative to the base plate 20 and movement of the measuring plates 50 through 54 relative to one another. In this instance, in lieu of the holding straps 21 through 26, cooperating Velcro materials 62 and 63 would be positioned on the top and bottom sides of each of the measuring plates, as 60 and 61. Similarly, the top surface of the base plate 20 would be provided with a Velcro surface, while the under surface of the sole plate 30 would be provided with the other complementary Velcro surface so that by placing one plate on another the Velcro materials themselves would serve to prevent relative movement of the various plates.

From the foregoing it can be seen there has been provided a novel foot elevation measuring device for determining the difference in leg length of an associated person. By providing both sole plate and base plate of predetermined thickness, and by providing intermediate measuring plates of predetermined thickness, the measuring device can be assembled until the proper elevation is achieved. By providing simple yet efficient means for holding the assembled measuring device to the person's shoe, the posture and gait of the person can be observed while standing and walking with the measuring device attached.

In construction, the sole and base plates are made of a rubber or crepe composition, preferably one that will provide sufficient stiffness to the plates while at the same time being light weight enough for easy handling and also being of a material that will accept a color dye to provide the different color codings for the different predetermined thicknesses of the measuring plates.

Because the materials are made of a light-weight composition, the weight thereof does not impose any undue burden on the patient during the measuring process.

Moreover, because of the nature of both the holding means and the binding means, there is sufficient adjustability in the measuring device to allow for elevating the device to a significant height, while at the same time the binding means are of sufficient length to accommodate shoes of various sizes, or can be used with a shoe off, whereby the measuring device has general utility, being limited neither to a man's or a woman's shoe sole, nor being limited in foot size.

The measuring device is of general utility and can be used in physical therapy rooms, rehabilitation clinics, hospitals, and doctors' clinics to substantially accurately measure the correctable elevation required to balance the length of the short leg, thereby allowing a permanent shoe buildup by a shoemaker or orthopedic shoe house in a fashion which will not require costly adjustments in the finished product.

While there have been described what are at present considered to be preferred embodiments of the invention, it will be understood that various modifications may be made therein and it is intended to cover in the appended claims all such modifications as fall within the true spirit and scope of the invention.

What is claimed is:

1. A device for measuring the relative difference in an individual's leg lengths in order to determine the amount of elevation required in the construction of an orthopedic shoe, to compensate for such difference, said device comprising a flat planar base plate of predetermined thickness; a flat planar sole plate of predetermined thickness and having a plan configuration similar to said base plate and being positionable in an overlying relationship relative thereto; at least one flat planar measuring plate of predetermined thickness and having a plan configuration similar to said base plate, said measuring plate being positionable between said base plate and said sole plate to increase the elevation of said measuring device by the predetermined thickness of said measuring plate; first, second and third pairs of holding straps respectively secured to said base plate adjacent to opposite ends thereof and intermediate the ends thereof, means for detachably connecting said pairs of holding straps to said sole plate to prevent relative movement of said sole plate, base plate and measuring plate; and binding means for securing said assembled sole plate and said base plate to the foot of the associated person, said binding means comprising first and second pairs of binding straps adapted to overlie the toe and ankle portions of the foot of the associated wearer, said binding straps being fixedly secured to said sole plate, a pair of heel binding straps secured to said sole plate and adapted to be connected behind the heel of the associated person, and means for detachably connecting the cooperating ends of respective pairs of binding straps, thereby to fixedly secure said measuring device to the foot of the associated person so as to allow said person to walk with the measuring device attached.

2. The measuring device set forth in claim 1 and further including a plurality of said measuring plates positionable between said base plate and said sole plate, at least one of said measuring plates being of a different predetermined thickness than other of said measuring plates.

3. The measuring device set forth in claim 2, wherein said one measuring plate is $\frac{1}{8}''$ thick and wherein said other measuring plates are of other thicknesses measured in $\frac{1}{8}''$ increments.

4. The measuring device set forth in claim 2, wherein said measuring plates are color coded such that plates of the same thickness are the same colors different in color from plates of other thicknesses.

5. The measuring device set forth in claim 1, wherein said means for detachably connecting said binding straps to the respective cooperating straps comprises a loop secured to one strap of each pair of straps and said cooperative strap includes, on the outer portion thereof, cooperating Velcro material to that of the remainder of said strap whereby pulling said strap through said loop permits additional tightening of said strap, and by folding said outer portion of said strap onto the remaining portion of said strap said strap is detachably connected.

6. A device for measuring the relative difference in an individual's leg lengths in order to determine the amount of elevation required in the construction of an orthopedic shoe, to compensate for such difference, said device comprising a flat planar base plate of predetermined thickness; a flat planar sole plate of predetermined thickness and having a plan configuration similar to said base plate and being positionable in an overlying relationship relative thereto; a flat planar measuring plate of predetermined thickness and having a plan configuration similar to said base plate, said measuring plate being positionable between said base plate and said sole plate to increase the elevation of said measuring device by the predetermined thickness of said measuring plate; holding means carried by said base plate for preventing relative movement of said sole plate and said measuring plate and said base plate; and binding means for securing said assembled base plate and measuring plate and sole plate to the foot of an associated person whereby such person can stand and walk thereon and whereby the elevation of said base plate and said sole plate can be computed and the correctable difference in elevation of the associated person's legs can be determined.

7. The measuring device set forth in claim 6, and further including a plurality of said measuring plates positionable between said base plate and said sole plate, at least one of said measuring plates being of a different predetermined thickness than other of said measuring plates.

8. The measuring device set forth in claim 7, wherein said one measuring plate is $\frac{1}{8}''$ thick and wherein said other measuring plates are of other thicknesses measured in $\frac{1}{8}''$ increments.

9. The measuring device set forth in claim 7, wherein said measuring plates are color coded such that plates of the same thickness are the same colors different in color from plates of other thicknesses.

10. The measuring device set forth in claim 6, wherein said holding means for preventing relative movement of said sole plate to said base plate comprises first, second and third pairs of holding straps respectively secured adjacent to opposite ends of said base plate and intermediate the ends thereof, and means for detachably connecting said pairs of holding straps to said sole plate, said means comprising a Velcro type material disposed on said sole plate and each of said holding straps having cooperative Velcro material on the overlying surfaces thereof whereby overlapping the Velcro material of said straps onto the cooperating material on said sole plate operates to detachably secure said holding straps to said sole plate, thereby to prevent relative movement of said sole plate, base plate and measuring plate.

11. The measuring device set forth in claim 6, wherein said binding means for securing said assembled sole plate and said base plate to the foot of the associated person comprises first and second pairs of binding straps adapted to overlie the toe and ankle portions of the foot of the associated wearer, said binding straps being fixedly secured to said sole plate, a pair of heel binding straps secured to said sole plate and adapted to be connected behind the heel of the associated person, and means for detachably connecting the cooperating ends of respective pairs of binding straps, thereby to fixedly secure said measuring device to the foot of the associated person so as to allow said person to walk with the measuring device attached.

12. The measuring device set forth in claim 11, wherein said means for detachably connecting said binding straps to one another comprises cooperating Velcro materials on each of said straps.

13. The measuring device set forth in claim 11, wherein said means for detachably connecting said binding straps to the respective cooperating straps comprises a loop secured to one strap of each pair of straps and said cooperative strap includes, on the outer portion thereof, cooperating Velcro material to that of the remainder of said strap whereby pulling said strap through said loop permits additional tightening of said strap, and by folding said outer portion of said strap onto the remaining portion of said strap said strap is detachably connected.

14. A device for measuring the relative difference in an individual's leg lengths in order to determine the amount of elevation required in the construction of an orthopedic shoe to compensate for such difference, said device comprising a flat planar base plate of predetermined thickness; a flat planar sole plate of predetermined thickness and having a plan configuration similar to said base plate and being positioned in an overlying relationship relative thereto; a first pair of holding straps secured to said base plate adjacent to one end thereof, and a second pair of holding straps secured to said base plate adjacent to the opposite end thereof, and means for detachably connecting said holding straps to said sole plate thereby to prevent relative movement of said sole plate and said base plate; and binding means for securing said assembled base plate and sole plate to the foot of an associated person whereby such person can stand and walk thereon and whereby the elevation of said base plate and said sole plate can be computed and the correctable difference in elevation of the associated person's legs can be determined.

15. The measuring device set forth in claim 14, wherein said holding means for preventing relative movement of said base plate and said sole plate also operates to prevent relative movement of said measuring plates and said base plate and said sole plate.

16. The measuring device set forth in claim 14, and further including a third pair of holding straps secured to said base plate, said third pair of holding straps being disposed about midway between said first and second pairs of holding straps, and means for detachably connecting said third pair of holding straps to said sole plate.

17. The measuring device set forth in claim 14, wherein said means for detachably connecting said pairs of holding straps comprises a Velcro-type material disposed on said sole plate and wherein each of said holding straps includes cooperative Velcro material on the overlying surfaces thereof whereby overlapping the Velcro material of said straps onto the cooperating material on said sole plate operates to detachably secure said holding straps to said sole plate.

* * * * *